United States Patent [19]
Kobayashi et al.

[11] Patent Number: 5,449,743
[45] Date of Patent: Sep. 12, 1995

[54] METHOD FOR RING OPENING POLYMERIZATION USING A HYDROLASE CATALYST

[75] Inventors: Shiro Kobayashi, 8-21, Yagiyama Minami 1-chome, Taihaku-ku, Sendai-shi, Miyagi-ken; Hiroshi Uyama, Sendai, both of Japan

[73] Assignees: Shiro Kobayashi, Miyagi; Shin-Etsu Chemical Co., Ltd., Tokyo, both of Japan

[21] Appl. No.: 184,912

[22] Filed: Jan. 24, 1994

[30] Foreign Application Priority Data

Jan. 29, 1993 [JP] Japan ................... 5-013327
Dec. 24, 1993 [JP] Japan ................... 5-326743

[51] Int. Cl.$^6$ ................... C08G 63/123; C08G 63/82
[52] U.S. Cl. ................... 528/355; 526/89; 526/204; 526/264; 526/266; 526/269; 526/271; 528/274; 528/312; 528/359

[58] Field of Search ............ 528/355, 312, 274; 526/89, 204

[56] References Cited

U.S. PATENT DOCUMENTS

| | | | |
|---|---|---|---|
| 4,110,411 | 8/1978 | Imanaka | 260/873 |
| 4,546,166 | 10/1985 | Niinomi | 528/60 |
| 4,642,267 | 2/1987 | Creasy | 428/413 |
| 4,820,743 | 4/1989 | Ishikawa | 521/137 |
| 5,219,731 | 6/1993 | Sih | 435/18 |

*Primary Examiner*—Fred Zitomer
*Attorney, Agent, or Firm*—McAulay Fisher Nissen Goldberg & Kiel

[57] ABSTRACT

In a method for ring opening polymerization in which the polymerization proceeds with the ring opening of a cyclic compound as a monomer, a hydrolase is used as a catalyst.

12 Claims, 4 Drawing Sheets

¹H NMR SPECTRUM (IN CDCl₃)

$^{13}$C NMR SPECTRUM (IN CDCl$_3$)

METHOD FOR RING OPENING POLYMERIZATION USING A HYDROLASE CATALYST

FIELD OF THE INVENTION AND RELATED ART STATEMENT

The present invention relates to a method for ring opening polymerization by the use of an enzyme catalyst, and it also relates to this enzyme catalyst for the ring opening polymerization.

The method for the ring opening polymerization is a polymerization technique in which the polymerization proceeds with the ring opening of a cyclic compound as a monomer to synthesize a polymer. At present, industrially important various synthetic polymers such as nylons, polyesters, polyethers, polyethyleneimines and polysiloxanes have been manufactured by the ring opening polymerization methods. In general, in order to cause the ring opening polymerization to proceed, it is necessary to add a catalyst to a reaction system. This catalyst acts on the cyclic compound to accelerate a ring opening reaction.

For cationic reactive monomers such as cyclic ethers, cyclic formals and cyclic imines, examples of the usable catalyst include Lewis acids such as $BF_3 \cdot O(C_2H_5)_2$, $SnCl_4$ and $AlCl_3$; alkyl halides such as alkyl chlorides and alkyl bromides; superstrong acids such as $CF_3SO_3H$; superstrong acid esters such as $CF_3SO_3R$ (R is an alkyl group); and cationic salts such as $R_3C^+PF_6^-$ and $R_3O^+BF_4^-$ (R is an alkyl group). Furthermore, for anionic reactive monomers such as cyclic siloxanes, lactams and cyclic acid anhydrides, examples of the usable catalyst include Li, Na, K, RCOONa, RONa and $R_2NLi$ (R is an alkyl group). In addition, for coordinated anionic reactive monomers such as cyclic ethers and lactones, examples of the usable catalyst include $(C_2H_5)_2Zn-H_2O$, $(C_2H_5)_2Zn-ROH$, $AlR_3$-acetylacetone-$H_2O$ (R is an alkyl group), and for metathetical reactive monomers such as cyclic olefins, examples of the usable catalyst include $MoCl_5$ and $WCl_6$.

However, these conventional catalysts have some problems. For example, (1) the effect of the catalyst is insufficient; (2) side reactions other than the polymerization take place; and (3) a part of the used catalyst is incorporated into a produced polymer, and in this case, the electrical insulating properties and the performance of the polymer deteriorate.

Moreover, in the ring opening polymerization by the use of the conventional catalyst, the main chain and the terminal structure of the polymer cannot be sufficiently controlled, and for this reason, such a conventional catalyst is unsuitable for a method for the preparation of a functional polymer.

OBJECT AND SUMMARY OF THE INVENTION

Therefore, an object of the present invention is to provide a method for ring opening polymerization which uses a specific catalyst and in which the main chain or the terminal structure of a produced polymer can be easily controlled, and the aforesaid specific catalyst is excellent in catalyst effect, capable of inhibiting side reactions, and capable of preventing the insulating properties and the performance of the polymer from deteriorating, even when the catalyst is incorporated into the produced polymer.

Another object of the present invention is to provide an enzyme catalyst for use in the above-mentioned polymerization method.

The present inventors have intensively investigated, and as a result, they have found that the above-mentioned problems can be solved by the use of a hydrolase as a catalyst for the ring opening polymerization. In consequence, the present invention has been attained by this knowledge.

For the achievement of the above-mentioned objects, the gists of the present invention reside in a method for ring opening polymerization in which the polymerization proceeds with the ring opening of a cyclic compound as a monomer by the use of a hydrolase as a catalyst, and an enzyme catalyst for the ring opening polymerization which comprises the hydrolase.

According to the present invention, the used catalyst is excellent in catalyst effect, inhibits side reactions, and prevents the insulating properties and the performance of the produced polymer from deteriorating, even if incorporated into the polymer. Additionally, in the present invention, the main chain or the terminal structure of the polymer can be easily controlled.

DETAILED DESCRIPTION OF PREFERRED EMBODIMENTS

Figure 1:
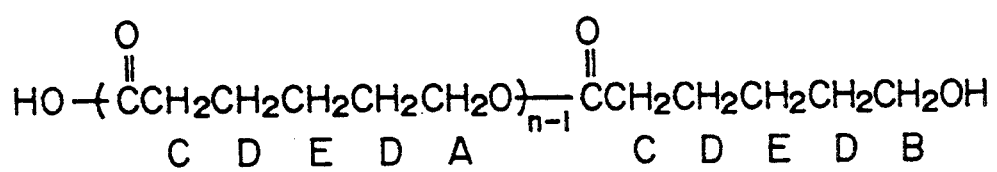
FIG. 1 is a graph showing the $^1H$ NMR spectrum of a produced polymer in Example 1 of the present invention.
Figure 1:
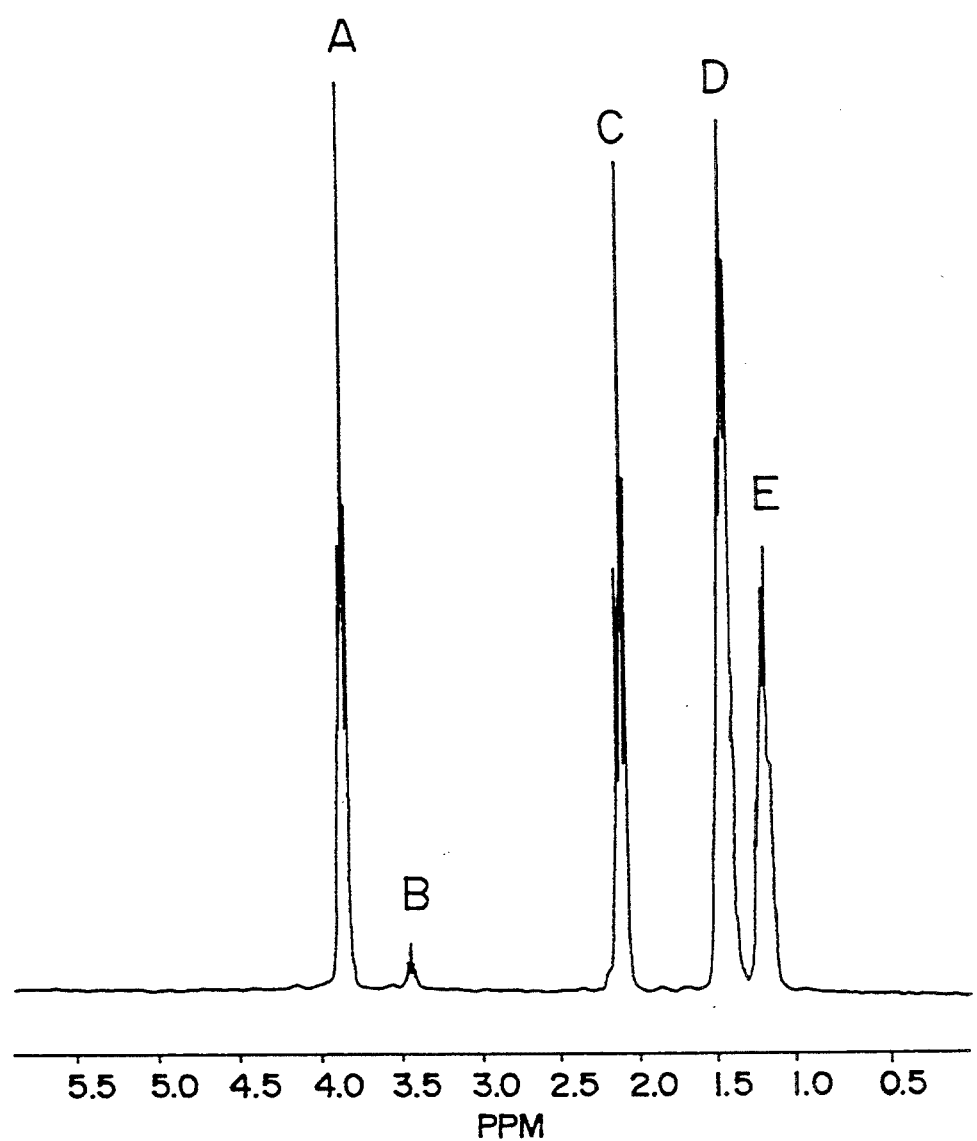

Ring opening homopolymerization means the ring opening polymerization of one kind of cyclic compound, and ring opening copolymerization means the ring opening polymerization of two or more kinds of cyclic compounds. In addition, ring opening addition condensation polymerization means the polymerization in which the ring opening polymerization proceeds by the repetition of addition reaction and condensation reaction, as in the following reaction of a cyclic anhydride and a diol:

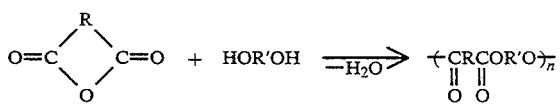

No particular restriction is put on the cyclic compound and the hydrolase to which the method for the ring opening polymerization of the present invention can be applied, so long as the cyclic compound can hydrolyze by the catalytic function of the hydrolase to open the ring, and the hydrolyzed product then reacts with the cyclic compound or the hydrolase in turn, whereby the polymerization can proceed.

Examples of the cyclic compound which can be used in the present invention include lactones such as β-propiolactone, β-butyrolactone, β-valerolactone, γ-butyrolactone, γ-valerolactone, γ-caprylolactone, ε-caprolactone, ε-stearolactone, ε-caprolactone, ε-caprylolactone and ε-palmitolactone; lactams such as β-propiolactam, γ-butyrolactam, γ-valerolactam, δ-valerolactam, ε-caprolactam and heptolactam; cyclic acid anhydrides such as succinic anhydride, maleic anhydride, glutamic anhydride and phthalic anhydride; cyclic carbonates such as ethylene carbonate and propylene carbonate; and lactides such as dilactide, diglycollide and diglyceride.

Examples of the hydrolase which can be used in the present invention include esterases such as lipase and azole esterase; proteases such as pepsin and trypsin; amidases such as aminase, cycloamidase, acid amidase and amidinase; and carbohydrases such as amylase and cellulase.

No particular restriction is put on the combination of the cyclic compound and the hydrolase, but for example, the esterases can be used in combination with the lactones and the cyclic carbonates, and the proteases and the acid amidase can be used in combination with the lactams. As is apparent from these combinations, the hydrolase can be preferably selected in accordance with the bonding style of the cyclic compound so as to cut its bond by a hydrolytic function.

No particular restriction is put on the amount of the hydrolase, but it is suitably to use 1 g or more of the hydrolase per mol of the cyclic compound which is the monomer.

Moreover, no particular restriction is put on a reaction temperature and a reaction time, but it is preferable that the reaction temperature is in the range of from 20° to 100° C. and the reaction time is 5 hours or more.

In the method for the ring opening polymerization regarding the present invention, the cyclic compound as the monomer and the hydrolase are contained as essential ingredients in the reaction system, but if necessary, a solvent such as toluene, chloroform, cyclohexanone, N,N'-dimethylformamide, dioxane or tetrahydrofuran may be added as a diluent for the reaction. In addition, for the purpose of controlling the terminal structure of an obtained polymer, various additives can be used, and typical examples of these additives include carboxylic acids such as caproic acid, benzoic acid, succinic acid and terephthalic acid; and amines such as hexylamine and tetramethylenediamine.

The feature of the method for the ring opening polymerization regarding the present invention is that the main chain and the terminal structure of the produced polymer can be easily controlled. For example, if ε-caprolactone is subjected to a ring opening polymerization by a conventional method, a polyester having hydroxyl groups at both the terminals is only produced, but according to the method for the ring opening polymerization of the present invention, a polyester having the hydroxyl group at one terminal and a carboxyl group at the other terminal is produced, and if a monocarboxylic acid is added to a reaction system, a polyester having the carboxyl group at one terminal and an ester group at the other terminal is produced. Furthermore, if a dicarboxylic acid is added to the reaction system, a polyester having carboxyl groups at both the terminals is produced. Thus, the terminal structure of the polymer can be easily carried out. The method for the ring opening polymerization of the present invention can be applied to ring opening copolymerization in which two or more kinds of cyclic compounds are reacted, and it can also be applied to ring opening addition condensation polymerization in which the ring opening polymerization proceeds by the repetition of addition reaction and condensation reaction, as in the reaction of a cyclic acid anhydride and a diol. In the method for the ring opening polymerization of the present invention, the enzyme is used as the catalyst, and therefore if a cyclic compound which is a racemic body is used as the monomer, the production of an optically active polymer can be expected by the selection of an asymmetric atom. Thus, the main chain of the polymer can be controlled.

Now, the present invention will be described in detail in reference to examples and comparative examples, but the scope of the present invention should not be limited to these examples.

EXAMPLE 1

Figure 2:
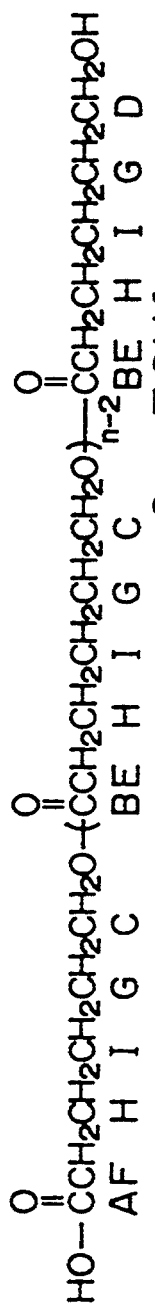
FIG. 2 is a graph showing the $^{13}C$ NMR spectrum of a produced polymer in Example 2 of the present invention.
Figure 2:
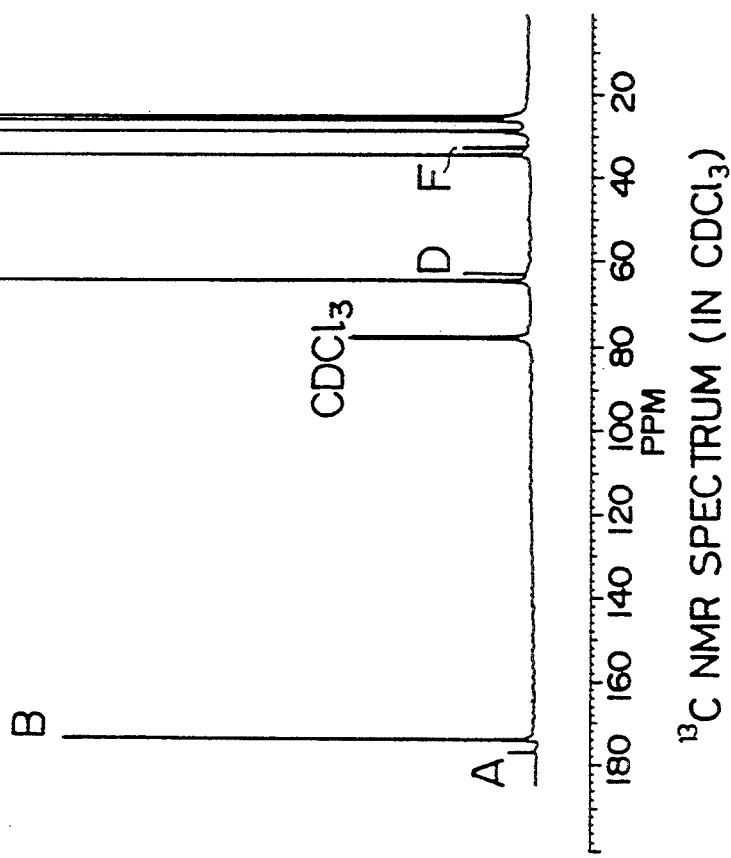

0.456 g (4 mmols) of ε-caprolactone (hereinafter abbreviated to "ε-CL") and 0.2 g of Lipase F (which was derived from *Pseudomonas fluorescens*) were placed in a 20 ml test tube, and this test tube was sealed, and then heated at 45° C. for 20 days. Afterward, the test tube was opened, and chloroform was added thereto and the resulting polymer was then extracted, followed by the concentration of chloroform. Next, hexane was added to the reaction system to reprecipitate the produced polymer, thereby isolating the polymer. FIGS. 1 and 2 show $^1$H and $^{13}$C NMR spectra of the thus produced polymer. It was confirmed from these NMR spectra that the produced polymer was a polyester having a carboxyl group and a hydroxyl group at its terminals. Furthermore, Table 1 shows the conversion ratio of the monomer as well as Mn (number average molecular weight), Mw (weight average molecular weight) and Mw/Mn of the produced polymer.

EXAMPLES 2 TO 10

Figure 3:
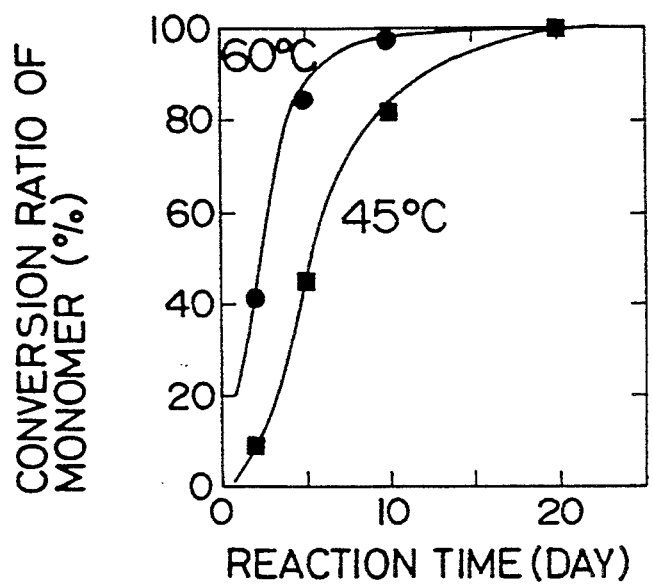
FIG. 3 is a graph showing the influence of a reaction time and a reaction temperature on a monomer conversion ratio.
Figure 4:
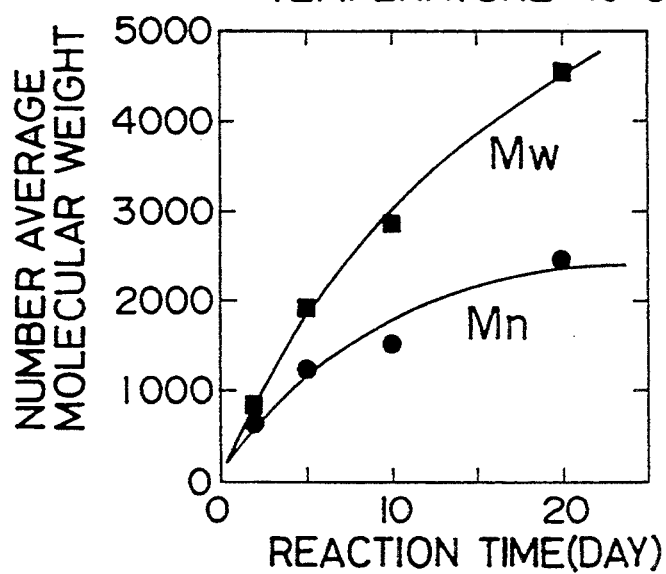
FIG. 4 is a graph showing the influence of the reaction time on the number average molecular weight and the weight average molecular weight of the produced polymer in polymerization at 45° C.
Figure 5:
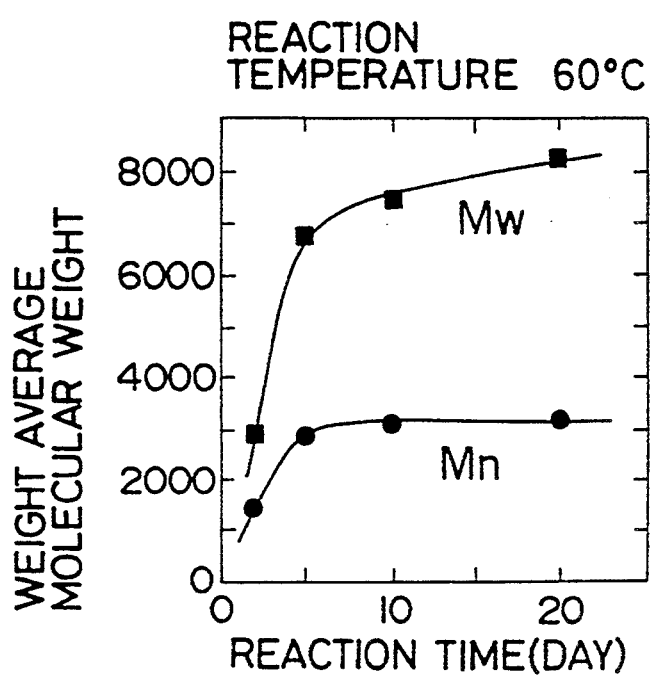
FIG. 5 is a graph showing the influence of the reaction time on the number average molecular weight and the weight average molecular weight of the produced polymer in the polymerization at 60° C.

Reaction was carried out by the same procedure as in Example 1 except that a reaction temperature and a reaction time were set as in Table 1, and the resulting polymer was then isolated. Next, the conversion ratio of the monomer as well as Mn, Mw and Mw/Mn of the produced polymer were measured. The results are shown in Table 1. On the basis of the results of Examples 1 to 10, the influence of the reaction temperature and the reaction time on the conversion ratio of the monomer as well as Mn and Mw of the produced polymer was shown in FIGS. 3, 4 and 5. These results indicate that the higher the reaction temperature is, the higher the polymerization rate is, and after the disappearance of the monomer, Mn is constant but Mw is apt to increase.

EXAMPLES 11 TO 16

Reaction was carried out by the same procedure as in Example 1 except that an additive was added in a ratio of 10 mol % to a monomer and a reaction temperature and a reaction time were set as shown in Table 1, and the resulting polymer was then isolated. Next, the conversion ratio of the monomer as well as Mn, Mw and Mw/Mn of the produced polymer were then measured.

The results are shown in Table 1. In order to inspect the structure of the produced polymer, NMR measurement was made. As a result, it was confirmed that in the case that amyl alcohol was added (Examples 11 and 12), the produced polymer had no amyl group at its terminals; in the case that caproic acid was added (Examples 13 and 14), the produced polymer had a caproic acid ester at its terminal; and in the case that amyl caproate was added (Examples 15 and 16), the produced polymer had neither an amyl group nor a carboxylate at its terminals.

EXAMPLES 17 TO 22

Reaction was carried out by the same procedure as in Example 1 except that PPL (Porcine Pancreas Lipase), Lipase B (which was derived from *Candida cylindracea*) and Lipase J (which was derived from *Rhizopus delemar*) were used as hydrolases and a reaction temperature and a reaction time were set as shown in Table 1, and the resulting polymer was then isolated. Next, the conversion ratio of the monomer as well as Mn, Mw and Mw/Mn of the produced polymer were then measured. The results are shown in Table 1.

EXAMPLES 23 TO 29

Reaction was carried out by the same procedure as in Example 1 except that δ-valerolactone (hereinafter abbreviated to "δ-VL") was used as a monomer and Lipase F or Lipase B was used as a hydrolase and a reaction temperature and a reaction time were set as shown in Table 1, and the resulting polymer was then isolated. Next, the conversion ratio of the monomer as well as Mn, Mw and Mw/Mn of the produced polymer were measured.

EXAMPLE 30

0.114 g (1 mmol) of ε-caprolactone, 0.100 g (1 mmol) of δ-valerolactone and 0.100 g of Lipase F were placed in a 20 ml test tube, and this test tube was sealed, and then heated at 60° C. for 10 days. Afterward, the test tube was opened, and chloroform was added thereto and the resulting polymer was then extracted. The conversion ratios of the respective monomers were measured by the use of a gas chromatograph, and as a result, both of them were 95% or more. The molecular weight of the produced polymer was measured by GPC, and the results were Mn=3200 and Mw/Mn=3.1. The structure of the polymer was inspected by $^1$H NMR, and thus it was indentified that the produced polymer was a polyester of a random copolymer containing both the components of ε-caprolactone and δ-valerolactone in equal amounts.

EXAMPLE 31

0.200 g (2 mmols) of succinic anhydride, 0.292 g (2 mmols) of 1,8-octanediol, 0.100 g of Lipase F and 5 ml of butyl ether were placed in a 20 ml test tube, and they were then stirred at room temperature for 3 days. Next, butyl ether was evaporated under reduced pressure, and chloroform was added thereto and the resulting polymer was then extracted. The chloroform solution was concentrated, and then poured into a large amount of methanol. The precipitated white powder was collected by filtration, and then dried. The molecular weight of the produced polymer was measured by GPC, and the results were Mn=1800 and Mw/Mn=1.6. It was identified by $^1$H NMR that the structure of the polymer was the following polyester:

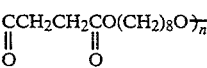

COMPARATIVE EXAMPLES 1 AND 2

All the same procedure as in Example 1 was carried out except that no catalyst was used and a reaction temperature and a reaction time were set as shown in Table 1, but the monomer was not polymerized at all. In consequence, any polymer was not obtained.

TABLE 1

| | Monomer | Catalyst | Additive | Reaction Temp. (°C.) |
|---|---|---|---|---|
| Example 1 | ε-CL | Lipase F | — | 45 |
| Example 2 | ε-CL | Lipase F | — | 45 |
| Example 3 | ε-CL | Lipase F | — | 45 |
| Example 4 | ε-CL | Lipase F | — | 45 |
| Example 5 | ε-CL | Lipase F | — | 60 |
| Example 6 | ε-CL | Lipase F | — | 60 |
| Example 7 | ε-CL | Lipase F | — | 60 |
| Example 8 | ε-CL | Lipase F | — | 60 |
| Example 9 | ε-CL | Lipase F | — | 75 |
| Example 10 | ε-CL | Lipase F | — | 90 |
| Example 11 | ε-CL | Lipase F | Amyl alcohol | 45 |
| Example 12 | ε-CL | Lipase F | Amyl alcohol | 75 |
| Example 13 | ε-CL | Lipase F | Caproic acid | 45 |
| Example 14 | ε-CL | Lipase F | Caproic acid | 75 |
| Example 15 | ε-CL | Lipase F | Amyl caproate | 45 |
| Example 16 | ε-CL | Lipase F | Amyl caproate | 75 |
| Example 17 | ε-CL | PPL | — | 45 |
| Example 18 | ε-CL | PPL | — | 60 |
| Example 19 | ε-CL | Lipase B | — | 45 |
| Example 20 | ε-CL | Lipase B | — | 60 |
| Example 21 | ε-CL | Lipase J | — | 45 |
| Example 22 | ε-CL | Lipase J | — | 60 |
| Example 23 | δ-VL | Lipase F | — | 45 |
| Example 24 | δ-VL | Lipase F | — | 60 |
| Example 25 | δ-VL | Lipase F | — | 60 |
| Example 26 | δ-VL | Lipase F | — | 60 |
| Example 27 | δ-VL | Lipase F | — | 60 |
| Example 28 | δ-VL | Lipase F | — | 60 |
| Example 29 | δ-VL | Lipase B | — | 45 |
| Comp. Ex. 1 | ε-CL | Lipase F | — | 45 |
| Comp. Ex. 2 | ε-CL | Lipase F | — | 60 |

| | Reaction Time (day) | Conversion Ratio of Monomer (%) | Mn | Mw | Mw/Mn |
|---|---|---|---|---|---|
| Example 1 | 20 | 100 | 2400 | 4500 | 1.9 |
| Example 2 | 2 | 9 | 620 | 840 | 1.4 |
| Example 3 | 5 | 45 | 1200 | 1900 | 1.6 |
| Example 4 | 10 | 83 | 1500 | 3000 | 2.0 |
| Example 5 | 2 | 41 | 1400 | 2900 | 2.1 |
| Example 6 | 5 | 84 | 2800 | 6800 | 2.4 |
| Example 7 | 10 | 97 | 3100 | 7500 | 2.4 |
| Example 8 | 20 | 100 | 3200 | 8200 | 2.6 |
| Example 9 | 10 | 99 | 5500 | 11000 | 2.0 |
| Example 10 | 10 | 100 | 6200 | 14000 | 2.3 |
| Example 11 | 10 | 83 | 1500 | 2800 | 1.9*[1) |
| Example 12 | 10 | 99 | 4200 | 8000 | 1.9*[1) |
| Example 13 | 10 | 57 | 940 | 1500 | 1.6*[2) |
| Example 14 | 10 | 99 | 1300 | 3000 | 2.3*[3) |
| Example 15 | 10 | 61 | 1000 | 1700 | 1.7 |
| Example 16 | 10 | 96 | 1800 | 4000 | 2.2 |

| | Monomer | Catalyst | Additive | Reaction Temp. (°C.) |
|---|---|---|---|---|
| Example 17 | 10 | 36 | 930 | 1200 | 1.3 |
| Example 18 | 10 | 93 | 1700 | 2700 | 1.6 |
| Example 19 | 10 | 77 | 1400 | 2300 | 1.6 |
| Example 20 | 10 | 97 | 2800 | 5700 | 2.0 |
| Example 21 | 10 | 5 | 650 | 720 | 1.1 |
| Example 22 | 10 | 19 | 810 | 1000 | 1.2 |
| Example 23 | 5 | 97 | 1000 | 1700 | 1.7 |
| Example 24 | 1 | 50 | 590 | 700 | 1.2 |

TABLE 1-continued

| | | | | | |
|---|---|---|---|---|---|
| Example 25 | 2 | 89 | 1000 | 1700 | 1.7 |
| Example 26 | 5 | 99 | 1500 | 3000 | 2.0 |
| Example 27 | 10 | 98 | 1500 | 2900 | 2.6 |
| Example 28 | 20 | 99 | 1500 | 4300 | 2.9 |
| Example 29 | 5 | 98 | 930 | 1300 | 1.4 |
| Comp. Ex. 1 | 10 | 0 | — | — | — |
| Comp. Ex. 2 | 10 | 0 | — | — | — |

*1) No amyl group was present at the terminal.
*2) The caproate was introduced as much as 40% into the terminal.
*3) The caproate was introduced as much as 90% or more into the terminal.

EXAMPLES 32 TO 38

Reaction was carried out by the same procedure as in Example 1 except that a monomer, an enzyme, a reaction temperature and a reaction time were set as shown in Table 2, and the resulting polymer was then isolated. Next, the conversion ratio of the monomer as well as Mn, Mw and Mw/Mn of the produced polymer were then measured.

TABLE 2

| | Monomer | Enzyme | Reaction Temp. (°C.) | Reaction Time (day) | Conversion Ratio of Monomer (%) | Mn | Mw | Mw/Mn |
|---|---|---|---|---|---|---|---|---|
| Example 32 | δ-CL | Lipase F | 60 | 10 | 16 | 1600 | 3800 | 2.4 |
| Example 33 | ε-CL | Lipase F | 60 | 10 | 54 | 670 | 900 | 1.3 |
| Example 34 | PDL | Lipase F | 60 | 10 | 76 | 2000 | 4300 | 2.2 |
| Example 35 | PDL | Lipase F | 75 | 10 | 100 | 7600 | 17000 | 2.2 |
| Example 36 | PDL | Lipase B | 45 | 10 | 25 | 1500 | 1900 | 1.3 |
| Example 37 | PDL | Lipase B | 60 | 10 | 49 | 4100 | 7000 | 1.7 |
| Example 38 | PDL | Lipase B | 75 | 10 | 86 | 19000 | 38000 | 2.0 |

δ-CL: δ-caprolactone
ε-HL: ε-heptanolactone
PDL: Pentadecanolactone

EXAMPLES 39 TO 42

Reaction was carried out by the same procedure as in Example 30 except that two monomers (Monomer 1 and Monomer 2) were set as shown in Table 3, and the resulting polymer was then isolated. Next, Mn, Mw and Mw/Mn of the produced polymer were then measured.

TABLE 3

| | Monomer 1 | Monomer 2 | Mn | Mw | Mw/Mn |
|---|---|---|---|---|---|
| Example 39 | ε-CL | PDL | 2100 | 5300 | 2.5 |
| Example 40 | ε-CL | δ-CL | 2700 | 7600 | 2.8 |
| Example 41 | ε-CL | ε-HL | 1400 | 2500 | 1.7 |
| Example 42 | ε-CL | DLA | 840 | 1400 | 1.7 |

DLA: Dilactide.

EXAMPLES 43 TO 49

Reaction was carried out by the same procedure as in Example 31 except that a cyclic acid anhydride, a glycol, a solvent and a reaction time were set as shown in Table 4, and the resulting polymer was then isolated. Next, the yield of the polymer as well as Mn, Mw and Mw/Mn of the produced polymer were measured.

TABLE 4

| | Cyclic Acid Anhydride | Glycol | Solvent | Reaction Time (day) | Yield (%) | Mn | Mw | Mw/Mn |
|---|---|---|---|---|---|---|---|---|
| Example 43 | SA | OG | Toluene | 3 | 42 | 1900 | 2900 | 1.5 |
| Example 44 | SA | OG | Toluene | 5 | 44 | 2900 | 4400 | 1.5 |
| Example 45 | SA | OG | Toluene | 10 | 57 | 2800 | 4600 | 1.6 |
| Example 46 | SA | OG | Benzene | 5 | 42 | 2300 | 3400 | 1.5 |
| Example 47 | SA | OG | i-propyl ether | 5 | 33 | 1000 | 1200 | 1.2 |
| Example 48 | SA | DEG | Toluene | 5 | 61 | 1800 | 2900 | 1.6 |
| Example 49 | SA | DOG | Toluene | 5 | 8 | 810 | 1100 | 1.4 |

SA: Succinic anhydride
OG: 1,8-octanediol
DEG: 1,10-decanediol
DOG: 1,12-dodecanediol

We claim:

1. A method for the ring opening polymerization of a cyclic compound polymer precursor comprising subjecting a cyclic compound selected from the group consisting of lactones, lactams, cyclic acid anhydrides, cyclic carbonates and lactides to ring opening polymerization conditions in the presence of a catalytically effective amount of hydrolase.

2. The method for ring opening polymerization according to claim 1 wherein a ring opening polymerization system is ring opening homopolymerization.

3. The method for ring opening polymerization according to claim 1 wherein a ring opening polymerization system is ring opening copolymerization.

4. The method for ring opening polymerization according to claim 1 wherein a ring opening polymerization system is ring opening addition condensation polymerization.

5. The method for ring opening polymerization according to claim 2 wherein the cyclic compound is a lactone and the hydrolase is a lipase.

6. The method for ring opening polymerization according to claim 4 wherein the ring opening addition condensation polymerization of a cyclic acid anhydride as the cyclic compound and a diol compound is carried out in the presence of a lipase as the hydrolase.

7. An enzyme catalyst for ring opening polymerization which comprises a hydrolase.

8. The method of claim 1, wherein the hydrolase is selected from the group consisting of esterases, proteases, amidases, and carbohydrases.

9. The method of claim 1, wherein a hydrolase is selected from the group consisting of lipase, azole esterase, pepsin, trypsin, amidase, cycloamidase, acid amidase, amidase, amylase and cellulase.

10. The method of claim 1, wherein the amount of hydrolase is at least 1 g per mol of cyclic compound.

11. The method of claim 1, wherein the ring opening polymerization is carried out at a temperature in the range from 20° to 100° C. for a reaction time of at least 5 hours.

12. A method for the ring opening polymerization of a cyclic compound polymer precursor comprising subjecting a cyclic compound selected from the group consisting of β-propiolactone, β-butyrolactone, β-valerolactone, γ-butyrolactone, γ-valerolactone, γ-caprylolactone, ε-caprolactone, δ-stearolactone, ε-caprolactone, ε-caprylolactone and ε-palmitolactone, β-propiolactam, γ-butyrolactam, γ-valerolactam, δ-valerolactam, ε-caprolactam and heptolactam, succinic anhydride, maleic anhydride, glutamic anhydride, phthalic anhydride, ethylene carbonate, propylene carbonate, dilactide, diglycollide and diglyceride to ring opening polymerization conditions in the presence of a catalytically effective amount of hydrolase.

* * * * *